United States Patent
Dharmesh Mahendrabhai et al.

(10) Patent No.: US 12,150,930 B2
(45) Date of Patent: Nov. 26, 2024

(54) ORAL LIQUID COMPOSITIONS OF ENZALUTAMIDE AND METHOD OF MANUFACTURING THEREOF

(71) Applicant: BDR Pharmaceuticals Int'l Pvt. Ltd., Gujarat (IN)

(72) Inventors: Shah Dharmesh Mahendrabhai, Mumbai (IN); Badiger Aravind Manappa, Gujarat (IN); Sharma Mukeshkumar Subhashchandra, Gujarat (IN); Trivedi Madhavkumar Dilipbhai, Gujarat (IN); Choksi Rakshit Ketanbhai, Gujarat (IN); Vora Pratik Ashwinbhai, Gujarat (IN); Agrawal Vijay Ashok, Gujarat (IN); Gandhi Prashant Kanaiyalal, Gujarat (IN); Panchal Nimitkumar Harishchandra, Gujarat (IN); Mori Nitin Merubhai, Gujarat (IN); Jayaswal Nilay Manikant, Gujarat (IN); Darji Hirenkumar Jitendrakumar, Gujarat (IN)

(73) Assignee: BDR Pharmaceuticals Int'l Pvt. Ltd., Panchmahals (IN)

( * ) Notice: Subject to any disclaimer, the term of this patent is extended or adjusted under 35 U.S.C. 154(b) by 0 days.

(21) Appl. No.: 18/362,431

(22) Filed: Jul. 31, 2023

(65) Prior Publication Data

US 2024/0058306 A1    Feb. 22, 2024

Related U.S. Application Data

(63) Continuation of application No. PCT/IN2022/050611, filed on Jul. 4, 2022.

(51) Int. Cl.
| | | |
|---|---|---|
| *A61K 31/4166* | (2006.01) | |
| *A61K 9/00* | (2006.01) | |
| *A61K 9/08* | (2006.01) | |
| *A61K 47/10* | (2017.01) | |
| *A61K 47/44* | (2017.01) | |

(52) U.S. Cl.
CPC ........ *A61K 31/4166* (2013.01); *A61K 9/0053* (2013.01); *A61K 9/08* (2013.01); *A61K 47/10* (2013.01); *A61K 47/44* (2013.01)

(58) Field of Classification Search
None
See application file for complete search history.

(56) References Cited

U.S. PATENT DOCUMENTS

| | | | |
|---|---|---|---|
| 7,709,517 B2 | 5/2010 | Sawyers et al. | |
| 2019/0209469 A1* | 7/2019 | Patel | A61K 47/10 |

FOREIGN PATENT DOCUMENTS

| | | |
|---|---|---|
| WO | 2014043208 A1 | 3/2014 |
| WO | 2015022349 A1 | 2/2015 |
| WO | 2015049650 A1 | 4/2015 |
| WO | 2018037310 A1 | 3/2018 |
| WO | 2019008426 A1 | 1/2019 |

OTHER PUBLICATIONS

Strickley, R.G., Solubilizing Excipients in Oral and Injectable Formulations, Pharm. Res., 21 (2004) pp. 201-230. (Year: 2004).*

* cited by examiner

*Primary Examiner* — Dominic Lazaro
(74) *Attorney, Agent, or Firm* — Husch Blackwell LLP

(57) ABSTRACT

The present invention relates to oral liquid formulations of Enzalutamide or pharmaceutically acceptable salt thereof and one or more pharmaceutically acceptable excipient. Further, the invention relates to providing an economical and technically advanced dosage form over existing dosage forms. In addition, the present invention also provides an improved process for preparation of Enzalutamide oral liquid formulation. The present invention further provides such compositions for the treatment of for the treatment of patients with metastatic castration-resistant prostate cancer who have previously received docetaxel.

3 Claims, No Drawings

ORAL LIQUID COMPOSITIONS OF ENZALUTAMIDE AND METHOD OF MANUFACTURING THEREOF

CROSS REFERENCE

This application is a continuation of PCT Application No. PCT/IN2022/050611 filed on Jul. 4, 2022, which claims the benefit of priority from Indian Patent Application 202121030404 filed on Jul. 7, 2021, the complete disclosures of which are incorporated herein by reference in their entirety.

FIELD OF THE INVENTION

The present invention relates to oral liquid formulations of Enzalutamide or pharmaceutically acceptable salt thereof and one or more pharmaceutically acceptable excipient. In addition, the present invention also provides an improved process for preparation of Enzalutamide oral liquid formulation. The present invention further provides such compositions for the treatment of for the treatment of patients with metastatic castration-resistant prostate cancer who have previously received docetaxel.

BACKGROUND OF THE INVENTION

Enzalutamide is non-steroidal anti-androgen (NSAA) agent used in the treatment of patients with metastatic castration-resistant prostate cancer. Structurally, Enzalutamide is represented as below:

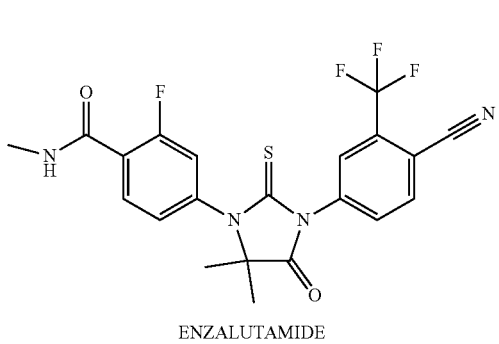

ENZALUTAMIDE (I)

Prostate cancer is a common cancer in men, especially in the US and in Europe. Prostate cancer is reported to grow slowly and can, if detected in an early stadium, be cured by the radical removal of the prostate. However, if not detected early prostate cancer can progress and result in an aggressive prostate cancer and the cancer cells may metastasize to other parts of the body and thus affect vitally important other organs, such the lymph nodes, lungs, bones and the gastrointestinal tract.

Enzalutamide is first disclosed in U.S. Pat. No. 7,709,517 and is marketed under the brand name of XTANDI®, which is a liquid-filled soft gelatin capsule for oral administration. The recommended dose of enzalutamide is 160 mg, which should be administered in the form of four capsules of 40 mg, daily. Each capsule contains enzalutamide dissolved in the solvent Labrasol® ALF, which is reported to contain caprylocaproyl macrogol-8 glycerides (caprylocaproyl polyoxyl-8 glycerides). With daily dosing regimen, steady state of enzalutamide is achieved after 28 days.

A possible handling of the disease depends on several individual conditions, such as age, general health, the extent of the cancer and possible metastasis. Thus, the decision whether or not to treat localized prostate cancer with a curative intent is a personal patient trade-off between the expected beneficial and harmful effects in terms of patient survival and the maintenance of a certain quality of life. According to the USFDA, XTANDI® is a liquid-filled soft gelatin capsule for oral administration comprising enzalutamide. The dosage form is reported to be used for the treatment of patients with metastatic castration-resistant prostate cancer.

WO2015/022349 discloses a formulation that contains enzalutamide in dissolved form. Further, invention uses a solvent that have HLB value responsible for forming water-in-oil type of emulsion. In preferred embodiment, the dosage form is a capsule, preferably a soft gelatin capsule.

WO 2014/043208 claims a formulation of enzalutamide that contains a spray dried particulate dispersion. Particulate dispersion having diameter of less than 50 μm, are compressed to form a tablet followed by encapsulation of the same.

WO2015/049650 exemplifies hard gelatin capsule formulation of enzalutamide and optionally in combination with Afuresertib. This combination is used in the treatment of cancer.

WO2014/0378517 reveals a solid dispersion containing formulation to improve solubility and absorption of enzalutamide. The above-mentioned invention also discloses that formulation and its method of preparation preferably in the form of tablet. This formulation has rapidly disintegrating property that leads to improvisation of bioavailability by providing the entire daily therapeutic dose of enzalutamide in a single dosage unit.

WO2019/008426 discloses novel compositions of enzalutamide preferably in hard gelatin capsule dosage form with pharmaceutically acceptable excipients and method of preparation thereof. The solution containing Labrasol® ALF and enzalutamide is sprayed on lactose anhydrous for surface adsorption during the granulation stage. Granulation is done by using fluidized bed process (FBP) or rapid mixing granulating method (RMG) or any other suitable granulating methods. The remaining acetone is evaporated in the drying stage of granulation, completing granulation process. Prepared granules are lubricated by microcrystalline cellulose (MCC) and Aerosil® 200 in the blender and are filled in a capsule. Hard gelatin capsule formulation of enzalutamide obtained in such a way exhibits superior performance with respect to dissolution data as well as product stability.

The present dose of XTANDI® is 160 mg, and it is administered orally once daily in the form of four capsules each containing 40 mg of active pharmaceutical ingredient, wherein the administration of XTANDI® is reported to be independent of food uptake. The above-mentioned composition comprising enzalutamide shows a dissolution behavior at acidic conditions, especially under simulated gastric fluid, which appears to be incomplete. In particular, the API does not remain dissolved but seems to precipitate. A further disadvantage is the recommended dose of 160 mg orally once daily, since this is related to an administration of four capsules once daily. Further, these capsules are reported to be very big due to the great amount of Labrasol® ALF necessary to keep the active pharmaceutical ingredient in solution. Due to its big size and the high number of capsules that has to be taken, this dosage form is difficult to swallow, in particular for older men, resulting in a poor patient compliance, especially in said important patient group.

Enzalutamide formulation is available in soft gelatin capsule. The present invention discloses a method of manufacturing oral liquid composition which does not require as much of sophisticated techniques. It uses reduced quantity of Labrasol® ALF compared to the existing prior arts. Therefore, it is significantly advanced technically and provides economic improvement over existing prior arts. Further, in existing prior art IIG limit for Labrasol® ALF is not within range of recommended daily dose by USFDA. This problem is also solved in the present invention which uses Labrasol® ALF within IIG limit range.

Soft gelatin capsules pose manufacturing challenges, where in particular, temperature and humidity have to be maintained and such formulations need dedicated manufacturing line. Soft gelatin capsules need special handling procedures during manufacturing, packaging and transporting the material, which makes the entire process more complicated and less economical. In contrast, the liquid oral solution of Enzalutamide provides a very simple and economical process. Further, oral liquid solution of Enzalutamide can be stored without special precautions of humidity which is essential in case of soft gelatin capsule storage as well as during manufacturing process.

OBJECTIVES OF THE INVENTION

The principal object of the present invention is to provide novel pharmaceutical formulations of Enzalutamide and pharmaceutically acceptable salt thereof in the form of oral liquid.

Another object of the present invention is to provide an economical and advanced dosage form over existing dosage form.

In yet another general object of the present invention is to provide a problem solution approach over the existing dosage form.

Still another aspect of the present invention is provided oral liquid dosage form which is in oral solution form with improved test having high patient complaints.

Yet another object of the present invention is to provide a process for preparation of oral dosage formulation of enzalutamide as an oral liquid.

Another object of the present invention is to provide liquid composition comprising Enzalutamide which is suitable for oral administration.

Yet another object of the present invention is provided composition which is used as medicament and process for preparation.

One more aspect of the present invention is to provide an oral dosage form with enhanced dissolution and stability profile.

SUMMARY OF THE INVENTION

Notwithstanding of wide research on Enzalutamide as reported in prior-art publications, there is an unmet need to develop a patient compliant oral liquid, here in specifically oral solution of pharmaceutical composition for Enzalutamide with technical advancement which provide fast dissolution for immediate action as well as good stability for at least more than two-year storage. This dosage form also increases patient compliance because patient feels difficulty specially for aged people and children's in taking conventional tablet or dispersible tablets when he or she is outdoor. Thus, the present invention has solved the problem that is present in the prior-arts as well as in the existing marketed formulations.

Accordingly, the present invention provides novel oral compositions of anti-cancer active pharmaceutical Ingredient preferably as liquid dosage form with pharmaceutically acceptable excipients and method of preparation thereof.

In one general aspect, an oral pharmaceutical composition comprising Enzalutamide as active pharmaceutical ingredient and one or more pharmaceutically acceptable excipients.

In one general aspect, a pharmaceutical composition as per the present invention is in the form of liquid formulation or liquid dosage.

In yet another aspect, a pharmaceutical composition as per the present invention comprises Enzalutamide and one or more pharmaceutically acceptable excipients wherein the composition is in the form of a solution.

In one embodiment of the present invention, wherein the active ingredient incorporated in the pharmaceutical composition comprises $D_{90}$ of particle size in the range of 1 to 100 microns, preferably, $D_{90}$ in the range of 21 to 80 microns.

In one of the embodiments, the pharmaceutical composition manufactured as per the present invention is an oral solution.

In yet another embodiment of the present invention, wherein the pharmaceutical composition manufactured is having particle size ranging from nanometer to micrometer, which results in to enhanced in-vitro dissolution profile.

Another embodiment according to the present invention, wherein the formulated product manufactured is having particle size ranging in nanometer or micrometer, which results in to enhanced in-vitro dissolution profile about 90% to 115%.

In yet another embodiment of the present invention, wherein the pharmaceutical composition manufactured by number of stages in manufacturing process including homogenization, stirring, heating, mixing and/or evaporation.

Additional embodiment according to the present invention is that the formulated product is a stabilized homogenous solution.

In yet another embodiment of the present invention, wherein pH of the pharmaceutical composition is in the range of 6.0 to 9.0, more preferably in the range of 6.4 to 6.9.

In another general aspect, a pharmaceutical composition as per the present invention comprises Enzalutamide or pharmaceutically acceptable salt thereof.

In another embodiment of the present invention, wherein the carrier molecules present in the pharmaceutical composition enhances absorption of Enzalutamide owing to their optimum lipophilic and hydrophobic properties.

Embodiments of the pharmaceutical composition may include Enzalutamide as an active ingredient with one or more selected from pharmaceutically acceptable excipients like diluent vehicles, Solubilizers, stabilizers/anti-oxidants, suspending/thickening agents, chelating/complexing agents, solubility enhancing agents, permeability enhancers, preservatives, glidants, active carriers, sweeteners, anti-caking agents, wetting agents, preservatives, buffering agents, flavoring agents and the like.

Another object of the present invention is to provide technically advanced patient-compliant dosage forms over existing dosage form and prior-arts.

The other object of the present invention is to provide reduced dose Enzalutamide formulations and thereby reducing the cost of final formulations by providing an economic significant dosage form over existing dosage form and prior-arts.

1. In general embodiment, pharmaceutical composition as per the present invention is in the form of an oral liquid comprising:
2. Taking one or more pharmaceutically acceptable vehicles and/or solubilisers;
3. adding one or more anti-oxidants with minimum temperature;
4. adding API (Active pharmaceutical Ingredient) to above prepared stage-1 and stage-2 solution under stirring until clear solution is formed;
5. adding one or more pharmaceutically acceptable sweeting agents and dissolve into the one or more solvents;
6. add one or more co-solvents in to above solution;
7. in above solution followed by addition of one or more flavouring agents and to make up homogenized volume followed by pH adjustment.
8. After continues homogenization process till the get clear solution.
9. Obtained clear solution and fill the solution in well closed cleaned bottle container.

In one embodiment of the present invention, pharmaceutical composition is in the form an oral solution comprising:
1. Take vehicle and/or solubiliser(s) as a solution part A and apply heating process and maintain the temperature;
2. Now adding anti-oxidant(s) in above-prepared solution and mixing the same through vortex or high-speed homogenizer or mechanical or sonicated or shear stress under the continuous process with minimum temperature of about 50° C.
3. Slowly add Enzalutamide in above prepared solution with maintaining temperature of solution under the continues homogenization process till get uniform dispersion;
4. Take sweetener agent(s) and dissolve into solvent which is solution part B, at that time in continuing of homogenization process add crushed solid part of flavouring agent;
5. Now, add solution part B into solution part A under continuous homogenization process till the get clear solution or uniform dispersion with maintaining temperature about about 50° C.;
6. Now add co-solvent in above prepared solution and homogenized till the get clear solution;
7. Once the solution gets cool down at room temperature add one flavouring agent under the homogenization process till get clear solution.
8. Obtained clear solution and fill the solution in well closed cleaned bottle container.

The details of one or more embodiments of the invention are set forth in the description below. Other features of the invention will be apparent from the description.

DETAILED DESCRIPTION OF THE INVENTION

The present invention will now be disclosed by describing certain preferred and optional embodiments, to facilitate various aspects thereof.

References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

The term "drug" or "active ingredient" or "active pharmaceutical ingredient (API)" herein refers to Enzalutamide or a pharmaceutically acceptable salt thereof.

The term "Enzalutamide" as used herein according to the present invention includes, Enzalutamide in the form of free base, a pharmaceutically acceptable salt thereof, amorphous, crystalline, any isomer, derivative, hydrate, solvate or prodrug or a combination thereof.

The term "oral dosage forms" as may include one or more of forms Syrup, oral solution, oral suspension, oral drop, oral emulsion, Mixture, Linctus, Elixir and like.

The term "drug solution" as used herein according to the present invention includes solution obtained by dissolving Enzalutamide or its pharmaceutically acceptable salt thereof in solvent and (or) mixture of solvents.

In accordance with the present invention, an oral pharmaceutical composition of Enzalutamide comprising of Enzalutamide as an active ingredient with pharmaceutically acceptable excipients in oral liquid dosage forms, preferably herein present invention in oral solution form.

Enzalutamide is a small molecule with no ionizable groups at biologically relevant pH; therefore, enzalutamide solubility is not affected by pH over the physiological range. Enzalutamide exhibits limited aqueous solubility (2.0 μg/mL at relevant pH range), high permeability across $CACO_2$ monolayers (mean apparent permeability coefficient (31× $10^{-6}$ cm/sec), and is not a substrate for P-glycoprotein. As it is having low solubility and high permeability, enzalutamide is considered a Biopharmaceutics Classification System (BCS) Class 2 drug substance.

In accordance with the present invention, an oral pharmaceutical composition of Enzalutamide comprising of Enzalutamide as an active ingredient with pharmaceutically acceptable excipients.

Excipients used in pharmaceutical solutions for oral administration of pharmaceutically acceptable Excipients in pharmaceutical formulations are physiologically inert compounds that are included in the formulation to facilitate the administration of the dosage form, e.g., pourability, palatability, to protect the formulation from issues regarding physical and chemical stability and to enhance the solubility of the therapeutic agent. Pharmaceutical solutions commonly contain a wide range of excipients, the details of which are provided below.

The term "pharmaceutically acceptable excipients" as used herein, refers to excipients those are routinely used in pharmaceutical compositions. The pharmaceutically acceptable excipients may comprise of diluents, vehicles, stabilizers/anti-oxidants, suspending/thickening agents, chelating/complexing agents, solubility enhancing agents, preservatives, glidants, sweeteners, anti-caking agents, wetting agents, preservatives, buffering agents, flavoring agents and combinations thereof.

At the time of preparation of the dosage form, the excipients of oral solution are mainly divided into following parts according to their uses in the manufacturing process (A) drug part, (B) stabilizers, (C) suspending/thickening agents, (D) Sweetening & flavoring agents, and (E) diluent vehicle. The list of excipients used are listed in tables below although it is not limited to the said excipients.

Fillers/Vehicles/Solubilizers referred in the present invention are the liquid bases which carry drug and other excipients in dissolved or dispersed state and can be selected from either aqueous vehicles or non-aqueous vehicles and Vehicles used in the formulation of liquid dosage forms may be aqueous (e.g., water, polyhydric alcohols, hydro-alcoholic solutions and buffers) or oily (e.g., vegetable or mineral oils, organic oily bases, emulsified bases etc). The choice of vehicle used depends on the nature and physicochemical properties of the active pharmaceutical ingredient (API) and the intended use of the formulation. Further, suitable Oily Vehicles/Solubilizers may include one or more of Capryl caproyl polyoxylglycerides (Labrasol® ALF), Capryl caproyl Polyoxyl-8 glycerides/PEG-8 caprylic/capric glycerides, polyoxyl35 castor oil (Kolliphor EL), Medium chain triglycerides (Labrafac Lipophile WL 1349) oleoyl polyoxyl-6 glycerides (Labrafil M1944 CS), Glyceryl Monolinoleate (Maisine CC), Polyoxyl 40 hydrogenated castor oil (Kolliphor RH 40), monopalmitate (Tween 60), sodium oleate, polyoxyethylene stearate, potassium oleate and combination thereof. The inventors of the present invention surprisingly found that polyoxyl 35 castor oil (Kolliphor EL) provide better solubility than other solublisers. The present invention comprises about 20.00% w/w to 97.00% w/w of solubliser of the total composition, preferably in the range of 25.00% w/w to 90.00% w/w of solubilizers of the total composition.

Antioxidants are added to some liquid dosage forms to delay or inhibit the oxidation process of molecules. Antioxidants act by getting preferentially oxidized or by blocking an oxidative chain reaction and therefore, antioxidants used in liquid dosage forms. Further, Suitable Antioxidants/stabilizers may include one or more of sodium sulphite, sodium metabisulphite, sodium formaldehyde sulphoxylate and ascorbic acid of antioxidants that may be used in oil-based solutions include and/or Butylated hydroxy anisole (BHA), Butylated hydroxytoluene (BHT), Ascorbic Acid, Vitamin E, Propyl gallate, Gallic acid, Potassium Metabisulfite, citric acid, sodium bisulphite, ascorbic acid, L-cysteine, magnesium bisulfite, tocopherol, ubiquinol, β-carotenes, uric acid, lipoic acid, thiourea, glutathione and the like. The inventors of the present invention surprisingly found that BHT & BHA provided better stability than other anti-oxidants. The present invention comprises about 0.01% w/w to 5.00% w/w of anti-oxidants or stabilizer of the total composition, preferably in the range of 0.01% w/w to 0.10% w/w of anti-oxidants or stabilizer of the total composition.

Solvents play key roles in designing drug delivery systems (DDSs). They are used as the reaction media in the preparation of DDSs and as vehicles for delivery of problematic drugs. The number of pharmaceutically acceptable solvents is limited and developing new green ones is of a great of interest. Specifically organic solvents are commonly used in the pharmaceutical industry as reaction media, in separation and purification of synthesis products and also for cleaning of equipment. This paper presents some aspects of organic solvents utilization in an active pharmaceutical ingredient and a drug product manufacturing process. Sometimes a drug must be applied as an ointment, swallowed in a syrup or injected as a liquid. Solvents are uniquely able to dissolve drugs safely and effectively into these medicinal formulations. Further, Solvent Suitable organic solvents for preparing binding solution may include one or more of water, organic solvents such as ethanol, isopropyl alcohol, acetone, propylene glycol, Glycerin and the like. Furthermore, the present invention comprises about 1.00% w/w to 25.00% w/w of solvents of the total composition, preferably 3.00% w/w to 20.00% of solvent of the total composition.

Co-solvents are primarily liquid components often used to increase the water solubility of drugs which do not contain ionizable group(s) and whose solubility can thus not be increased by pH adjustment. They work by reducing the interfacial tension between Co-solvents are partially polar due to the presence of hydrogen bond donors and/or acceptors, thus ensuring miscibility with water. The selection of a co-solvent depends on a number of factors, including the solubility and stability of drug substance in the vehicle and toxicity of the vehicle. Most water-miscible organic liquids are however toxic and only a few are used as co-solvents in pharmaceutical solutions. Each co-solvent is characterized by an acceptable concentration range, which cannot be exceeded without incurring biological damage. The use of co-solvents in parenteral as well as oral solid formulations has been limited by the uncontrolled precipitation of the drug substance upon dilution in aqueous/biological media which results in embolism or necrosis at the injection site. In vitro and in vivo models are available to evaluate the safety of co-solvent excipients. Further, suitable co-solvents or vehicles may include one or more of Labrafac lipophile WL 1349/Sorbitol solution/Castor Oil/Soyabean Oil Glycerol monolinoleate EP/Glyceryl monolinoleate NF, Propylene Glycol, glycerol, propylene glycol, the low molecular weight PEGs, Polyethylene glycol 4000 (PEG 400) and the like. Furthermore, the present invention comprises about 1.00% w/w to 45.00% w/w of co-solvents of the total composition, preferably 10.00% w/w to 39.00% of solvent of the total composition.

Surprisingly, when the inventors of the present invention combined the solvents First solvent is cremophore EL, second solvent is PEG 400 and specially third solvent is ethanol in optimum concentration in trio-combination with other excipients, the bad flavouring or not controlled flavouring problem was solved and optimum solution with good flavouring and controlled condition was also achieved. Thus, synergistic effect was observed by the inventors of the present invention by combining these two inactive ingredients. In addition, this excipient and/or solvents combination also provided rapid dissolution which is prime requirement of oral route. Furthermore, this combination of excipients and/or solvents also improved mouthfeel with flavouring than other excipients which is also the requirement for the oral route.

Sweeteners are employed in liquid pharmaceutical dosage forms intended for oral administration specifically to increase the palatability of the therapeutic agent. Further, suitable sweeteners may include one or more of Neohesperidine DC/Neotame, Sucralose, Aspartame, Neotame, Saccharin Sodium, Sucrose, Glycyrrhiza glabra, acesulfame potassium, sorbitol, mannitol, xylitol, high fructose corn syrup and the like. Furthermore, here in the present invention comprises about 0.01% w/w to 20.00% w/w of sweeteners of the total composition, preferably 0.04% w/w to 10.00% w/w of sweetener of the total composition.

Generally, flavoring agents are vital excipients for chewable tablets, oral disintegrating tablets, dispersible tablets, oral solutions, and oral suspensions to mask the unpleasant smell as well as taste and to make the product more palatable, thus increasing patient compliance. Further, suitable flavouring agents may include one or more of Sweet orange, Mint Flavour, Garden Mint, Orange flavour, Levomenthol and derivatives thereof, peppermint, grapefruit, orange, lime, lemon, mandarin, pineapple, strawberry, raspberry, mango, passion fruit, kiwi, apple, pear, peach, apricot, cherry, grape, banana, cranberry, blueberry, black currant, red currant, gooseberry, lingon berries, cumin, thyme, basil, camille, valerian, fennel, parsley, chamomile, tarragon, lavender, dill, bargamot, salvia, aloevera balsam, spearmint, piperine, eucalyptus, and the like. Furthermore, the present invention comprises about 0.05% w/w to 20.00% w/w of flavouring agents of the total composition, preferably 0.20% w/w to 7.00% w/w of flavouring agent of the total composition.

One embodiment of the present invention may include a pharmaceutical composition comprising about 1.00% w/w to 30.00% w/w of Enzalutamide, preferably 1.00% w/w to 5.00% w/w with pharmaceutically acceptable excipients.

The present invention faced challenges during development of formulation and finding the solutions of problems which are describe below it:

1. Selection of Excipients for the Present Invention:

During the selection of excipients for formulation of Enzalutamide oral solution, first it is required to select the excipients which are not covered by patent of Enzalutamide capsules and also excipients need to meet IIG limits and useful for product development. Based on this various solubilizers/solvents and cosolvents were selected to study Enzalutamide API solubility.

In the present invention selection of Solubilizers based on different trials which are like Labrafac Lipophile WL-1349, Labrafil M1944 Cs, Maisine CC, Kolliphor RH 40, Tween 80, Castor Oil, Migloyl 812 etc.

Further, here in the present invention selection of Co-solvents also based on trials and experiments which are Propylene glycol, Polyethylene glycol 400, Poly ethylene glycol 200, Ethanol, Glycerine, Maisine CC etc.

From above listed excipients API solubility study was performed from that combination of Kolliphor RH 40 with Ethanol and Polyethylene 400 showed complete and stable solubility of API. Based on the API solubility study combination of Kolliphor RH 40 with Ethanol and Polyethylene 400 was taken for further study.

Combination of Kolliphor RH 40 with Ethanol and Polyethylene 400 showed the API was completely dissolved and absence of any recrystallization upon storage/Stability study/ageing of solution.

2. Ethanol Level and Addition Studies for the Present Invention:

In this formula ethanol addition step was selected after immediate addition of API, the step was chosen based on taken small trial observations that before addition of API at the initial stage, during last step addition into formulation etc. also ethanol is helpful to solubilize the API into formulation.

During the solution preparation stage, applying heat of 45° C.±5° C. during procedure so if we add ethanol at the initial stage there may be chances of evaporation of some amount of ethanol due addition time and soluble time of another listed excipients needs to add before API and also due to heating stage applied, so in that case the API solubilizing time or dissolution time may be increased or chances of recrystallization.

During last stage addition of API into formulation here the observation was the processing time was delayed due to API solubilize/dissolve API completely into solution. After addition of API into solution and then addition of ethanol part into solution, so the observation was approx. 80% of API was solubilized properly during procedure and processing time was saved, so this step was finalized for ethanol addition.

3. After Completion of Studies Finalized Concentration of Ethanol as Best Solvent for the Present Formulation:

As per taken trials with diff. concentrations of ethanol here 7.08% concentration ethanol showed best results according to formulation with proper API solubility, no recrystallization during storage/aging of solution and no Microbial growth was observed.

4. Selection of Sweeteners and Flavouring Agents for the Present Invention:

The inventors of the present invention who are skilled person in the field of formulation, they were conducted several placebo trials and were taken and tested to proper selection of sweeteners and flavouring agents then finalize. Kolliphor RH 40 is having warm mouth feel effect and oily taste in nature, so to minimize that taste several sweeteners and flavouring agents were added and tested placebo. E.g., Of Sweeteners: Sucrose, Neohesperidine, Aspartame, liquid glucose, Neotame. From all the above-mentioned excipients Neotame showed good sweeting effect also easily soluble and not showed any recrystallization.

Further, E.g., of Flavouring agents: Peppermint flavour, orange flavour, Strawberry flavour, Raspberry Flavour. From all mentioned excipients Peppermint flavour showed satisfying effect due to its cooling mouth feel effect and with Neotme (Sweeteners) the taste of peppermint flavour was satisfactory. In addition of that also L-menthol was selected to formulation which was used as helping hand for pepper mint flavour for proper cooling mouth feel effect to minimize the warm feel effect and oily taste of Kolliphor RH 40.

The invention will be further described with respect to the following examples; however, the scope of the invention is not limited thereby. All percentages stated in this specification are by weight, unless otherwise specified. While the present invention has been described in terms of its specific embodiments, certain modifications and equivalents will be apparent to those skilled in the art and are intended to be included within the scope of the present invention. The following examples are provided for illustrative purpose only and these examples are in no way limitative on the present invention.

EXAMPLES

Example-1: Enzalutamide Oral Solution with Different Excipients

| Sr. No | Ingredients | % w/w |
|---|---|---|
| 1. | Enzalutamide (Micronized API) | 3.20 |
| 2. | Caprylocaproyl polyoxylglycerides (Labrasol ALF) | 72.00 |
| 3. | Butylated hydroxyanisole (BHA) | 0.01 |
| 4. | Butylated hydroxyanisole (BHA) | 0.01 |
| 5. | Sweet Cherry flavor | 1.10 |
| 6. | Neotame | 0.04 |
| 7. | Neohesperidine | 0.30 |
| 8. | Levo Menthol | 0.07 |
| 9. | Methyl Paraben | 0.18 |
| 10. | Propylparaben | 0.02 |
| 11. | Labrafac lipophile WL 1349 | 14.07 |
| 12. | Propylene glycol | 9.00 |
| | Total | 100.00 |

Process for Preparation:
1) Take Labrasol ALF in a beaker and name the breaker as A. start the heating process and maintain, the temperature of solution to 45° C.
2) Now add B.H.A and B.H.T in breaker A and stir until it gets dissolve completely, then add Propyl paraben & Methyl paraben for dissolve under continuous homogenization process with temperature of 45° C. with homogenization speed.
3) Now Slowly add API in above solution with maintaining temperature of solution about 45° C. under continuous homogenization process till it gets clear solution.

4) Take Neotame and Neohespiridine and individually dissolve into beaker A solution with continuous homogenization with maintain the temperature of 45° C., Then crush the solid part of Levo menthol and dissolve into it with homogenization speed.
5) Then take Labrafac Lipophile WL 1349 MCT oil in separate beaker and name as B.
6) Add solution B into solution A under continuous homogenization process till it gets clear solution with maintaining temperature of 45° C. with homogenization speed.
7) Stop the heating process and add Propylene glycol into resultant solution with continuous homogenization process till to get clear solution.
8) Once the solution gets cool down at room temperature then add sweet cherry flavour under homogenization process till get clear solution.

Observation:

After compellation of the above process or experiment the inventors of the present invention, test the obtained solution by different analytical method and check its dissolution profile and stability and obtained the results which was appears to be not virtuous compare to the reference standard data.

Example-2: Selection of Solubilizers/Solvents/Co-Solvents for Enzalutamide Oral Solution

| Sr. No | Ingredients | % w/w |
|---|---|---|
| 1 | Enzalutamide | 2.60 |
| 2 | Medium chain triglycerides (Labrafac Lipophile WL 1349) | 32.47 |
| 3 | Oleoyl polyoxyl-6 glycerides (Labrafil M1944 CS) | 64.94 |
|  | Total | 100.00 |

Process for the Preparation:
1. Dispensed quantity of medium chain triglycerides was taken and Enzalutamide was added into it and mixing was done with help of stirrer/homogenizer.
2. Dispensed quantity of Oleoyl polyoxyl-6 glycerides was taken and added into above solution and continue mixing procedure till Enzalutamide was dissolved completely.

Observations:

Enzalutamide was not dissolved completely during process and later on heating step was applied to 1 hour at 45° C. to dissolve the Enzalutamide if could be help it out but Enzalutamide was not dissolved completely and settled at bottom part.

Example-3: Selection of Solubilizers/Solvents/Co-Solvents for Enzalutamide Oral Solution

| Sr. No | Ingredients | % w/w |
|---|---|---|
| 1 | Enzalutamide | 2.60 |
| 2 | Oleoyl polyoxyl-6 glycerides (Labrafil M1944 CS) | 64.94 |
| 3 | Glyceryl Monolinoleate (Maisine CC) | 32.47 |
|  | Total | 100.00 |

Process for the Preparation:
1. Dispensed quantity of Glyceryl Monolinoleate was taken and Enzalutamide was added into it and mixing was done with help of stirrer/homogenizer during this procedure heating stage was applied at 45° C.
2. Dispensed quantity of Oleoyl polyoxyl-6 glycerides was taken and added into above solution and continue mixing procedure till Enzalutamide was dissolved completely.

Observations:

During the procedure because of applied heating process, initially Enzalutamide was observed dissolved around 10-20% but in continuation of process API was not fully dissolved after increasing the quantity of Glyceryl Monolinoleate and Oleoyl polyoxyl-6 glycerides step by step also processing time but Enzalutamide was not dissolved properly.

Example-4: Selection of Solubilizers/Solvents/Co-Solvents for Enzalutamide Oral Solution

| Sr. No. | Ingredients | % w/w |
|---|---|---|
| 1 | Enzalutamide | 2.96 |
| 2 | Polyoxyl 40 hydrogenated castor oil (Kolliphor RH 40) | 46.21 |
| 3 | Glyceryl Monolinoleate (Maisine CC) | 27.73 |
| 4 | Ethanol | 4.62 |
| 5 | propylene glycol | 18.48 |
|  | Total | 100.00 |

Process for the Preparation:
1. Dispensed quantity of Polyoxyl 40 hydrogenated castor oil was taken and started heating with maintained temperature of 45° C. of product. Further, Dispensed quantity of glyceryl monolinoleate was added to material of above step under stirring mixing/homogenization process.
2. Enzalutamide was added to above step of material under stirring/homogenization process. Further, then dispensed quantity of Ethanol was added to above step of material and continued process of stirring/homogenization then added dispensed quantity of propylene glycol and continued the process till Enzalutamide was dissolved.

Observations:

During the process it was observed that homogenized dispersion was observed but for clear solution frequently ethanol was added and continued process to check the solubility but about 50 to 70% of Enzalutamide was dissolved and remaining was as such so additional co-solvent propylene glycol was added to formulation and continued the procedure with maintain product temp. But at the end of process around 20 to 30% of Enzalutamide was not dissolved and remained as such after increased the processing time of stirring/homogenizing.

Example-5: Final Selection of Solubilizers/Solvents/Co-Solvents for Enzalutamide Oral Solution

| Sr. No. | Ingredients | % w/w |
|---|---|---|
| 1 | Enzalutamide | 3.20 |
| 2 | Polyoxyl 35 castor oil (Kolliphor EL) | 51.50 |

| Sr. No. | Ingredients | % w/w |
|---|---|---|
| 3 | Ethanol | 7.08 |
| 4 | Polyethylene glycol 400 | 38.22 |
| | Total | 100.00 |

Process for the Preparation:
1. Polyoxyl 35 castor oil was taken and started heating process with maintaining product temp. of 45° C. with observed the physical property that it was converted from light hazy to clear solution state then proceed for further.
2. Then Enzalutamide was added to material of above step under stirring process/homogenization and continued the process for 30 to 50 minutes. Then ethanol was added to material of above step under stirring process/homogenization and continued the process for 20 to 30 min under stirring/homogenization.
3. Finally PEG 400 was added to material of above step and continued the stirring/homogenization process with maintained product temp. Of 45° C. till the API was dissolved completely.

Observations:
1. Initially the inventors of the present invention have proceeded for the 1st and 2nd step but due to property of Kolliphor EL 40 that it remains hazy at room temperature. So, Enzalutamide was not dissolved properly and not became a clear solution. So, we have repeated same procedure with giving the heating stage with maintained product temp. of 45° C. o 55° C. and observed that Kolliphor EL was easily converted to clear solution after giving temperature above 45° C. and remained clear.
2. After addition of Enzalutamide and continued the process approx. 50% of Enzalutamide was dissolved at this stage and when added ethanol into the formulation and continued the process and observed that ethanol helped to dissolve almost Enzalutamide and after addition of PEG 400 and continued the process and observed that Enzalutamide was dissolved completely and forms a clear solution.
3. This solution was then further observed for 1 month and it was clear in state and no layer separation as well as no recrystallization was appeared. Hence this composition was finalized for finalization of Solubilizers/Solvents/Co solvents.

Example-6: Selection of Flavouring Agent for Enzalutamide Solution

| Sr. No. | Ingredients | % w/w |
|---|---|---|
| 1 | Enzalutamide | 3.20 |
| 2 | Polyoxyl 35 castor oil (Kolliphor EL) | 51.50 |
| 3 | Ethanol | 7.08 |
| 4 | Polyethylene glycol 400 | 37.02 |
| 5 | Peppermint flavour | 1.20 |
| | Total | 100.00 |

Process for the Preparation:
1. Polyoxyl 35 castor oil was taken and started heating process with maintaining product temp. of 45° C. with observed the physical property that it was converted from light hazy to clear solution state then proceed for further.
2. Then Enzalutamide was added to material of above step under stirring process/homogenization and continued the process for 30 to 50 minutes. Then ethanol was added to material of above step under stirring process/homogenization and continued the process for 20 to 30 min under stirring/homogenization.
4. Then PEG 400 was added to material of above step and continued the stirring/homogenization process with maintained product temp. Of 45° C. till the Enzalutamide was dissolved completely.
5. Finally added Peppermint flavour as a flavouring agent under the homogenization process till get clear solution.

Observations:
From above compositions to finalize flavour to formulation various oil soluble flavouring agents were selected, from that placebo solution was prepared of above composition and checked with individual flavouring agent with increasing concentration of flavourants and from stated flavourants the taste as well as smell of solution was found satisfactory with Peppermint flavour hence peppermint flavour was finalized for this composition.

Example-7: Selection of Sweetener for Enzalutamide Solution

| Sr. No. | Ingredients | % w/w |
|---|---|---|
| 1 | Enzalutamide | 3.20 |
| 2 | Polyoxyl 35 castor oil (Kolliphor EL) | 51.50 |
| 3 | ethanol | 7.08 |
| 4 | Polyethylene glycol 400 | 36.61 |
| 5 | Neohesperidine dihydrochalcone | 0.30 |
| 6 | Neotame | 0.04 |
| 7 | L menthol | 0.07 |
| 8 | Peppermint flavour | 1.20 |
| | Total | 100.00 |

Process for the Preparation:
1. Polyoxyl 35 castor oil was taken and started heating process with maintaining product temp. of 45° C. with observed the physical property that it was converted from light hazy to clear solution state then proceed for further.
2. Then Enzalutamide was added to material of above step under stirring process/homogenization and continued the process for 30 to 50 minutes.
3. Then ethanol was added to material of above step under stirring process/homogenization and continued the process for 20 to 30 min under stirring/homogenization.
4. Then PEG 400 was added to material of above step and continued the stirring/homogenization process with maintained product temp. Of 45° C. till the Enzalutamide was dissolved completely.
5. Then added Peppermint flavour as a flavouring agent under the homogenization process till get clear solution.
6. Finally added Neohesperidin dihydrochalcone and/or Neotame and/or L menthol as a sweetener agent under continuous the homogenization process till gets clear solution.

Observations:
1. From above compositions various sweeteners were selected and tasted with placebo trials and initially found that with Neotame and Neohesperidine the taste of solution was found satisfactory and remaining sweeteners were not dissolved into solutions as well as recrystallization and no proper sweetening effect was observed.
2. Therefore, combination of Neotame and Neohesperidine dihydrochalcone were selected for final composition but later on it was found due to Neohesperidine the solution was appeared mild yellowish to yellowish in colour.
3. Then again trial was taken of same composition and neohesperidin was removed and added L menthol to solution and tasted placebo and found that solution was not appeared in yellowish colour as well as due to addition of L Menthol into solution the warm effect of Kolliphor EL was mostly minimized and suited perfectly with combination of Peppermint flavour and L menthol with Neotame as sweeteners. Also, physical examination study was taken upon different duration and found that the solution was as it is as initial, only mild yellowish colour of solution was observed but that was due to yellowish colour property of Kolliphor EL.

Example-8: Enzalutamide Oral Solution

| Sr. No. | Ingredients | % w/w |
|---|---|---|
| 1 | Enzalutamide | 3.20 |
| 2 | Polyoxyl 35 castor oil (Kolliphor EL) | 51.50 |
| 3 | Butylated Hydroxy anisole (BHA) | 0.01 |
| 4 | Butylated Hydroxytoluene (BHT) | 0.01 |
| 5 | Peppermint Flavour | 1.20 |
| 6 | Neotame | 0.04 |
| 7 | L menthol | 0.07 |
| 8 | Ethanol | 7.08 |
| 9 | Polyethylene Glycol 400 | 36.89 |
|  | Total | 100.00 |

Process for the Preparation:
1) Take Polyoxyl 35 castor oil (Kolliphor EL) in a beaker and It part A or Solution A. Then start the heating process and maintain, the temperature of solution to 50° C. and observe the Kolliphor EL gets change of light hazy to clear solution, then proceed for further.
2) Now add B.H.A and B.H.T in breaker (Solution A) and stir it under Continuous homogenization process with maintaining the temperature of product about 50° C. with Homogenization speed.
3) Now Slowly add Enzalutamide (API) in above solution with maintaining the temperature of solution about 50° C. under Continuous homogenization process till to the get uniform dispersion with Homogenization speed.
4) Take Neotame and dissolve into Ethanol with Continuous homogenization in another beaker, then add crushed solid part of L-Menthol into same beaker and dissolve into it, it is Part-B (Solution B) with Homogenization speed.
5) Add solution B into solution A under continuous homogenization process till it gets clear solution or uniform dispersion with maintaining temperature of 50° C. With Homogenization speed.
6) Now add Polyethylene glycol 400 (PEG 400) into resultant solution with Continuous homogenization process till to get clear solution. *Homogenization speed:
7) Once the solution gets cool down at room temperature then add peppermint flavour under homogenization process till get clear solution with Homogenization speed.
8) The Resultant solution appears as light yellowish clear solution.
9) Then obtained clear solution fill into the clean and closed bottle container.

Observation:
After completion of all the experiments and/or different trials the present invention obtained clear solution and also tested with different analytical method. Further, the inventors of the present invention get good results of the present invention like the good stability, good dissolution profile as well as obtained good physio-chemical property which are describe below it.

DISSOLUTION STUDY FOR THE PRESENT INVENTION

Dissolution profile of the product of present invention was studied. Dissolution study of the pharmaceutical dosage form the present invention was carried out by FIPLC.

Dissolution profile of the pharmaceutical dosage form as per the present invention was carried out using USP apparatus type II (paddle).

In this, 0.3% cetyltrimethylammonium bromide (CTAB) in 0.1 N HCl of 900 ml was used as dissolution media at 50 RPM for 30 min of time duration at (37±0.5)° C. In this acetonitrile (ACN), triethylamine and dihydrogen potassium phosphate reagents were used as per mobile phase preparation.

Dissolution media was prepared by adding 8.5 ml concentrated HCl into 1000 ml of water. In this solution, 3.0 g of CTAB was dissolved and mixed well.

Standard solution was prepared by adding about 17.5 mg of enzalutamide into 100 ml volumetric flask. In that, 25 ml of ACN was dissolved and diluted with ACN to volume. From this solution, 2 ml of solution was transferred to a 100 ml volumetric flask and diluted with dissolution medium to volume. The standard solution was found stable at 25° C. for 27 h. Sample solution was prepared by adding a 5 ml sample of the present invention in 900 ml of dissolution medium. Further, 2.0 ml of this solution was diluted with 100 ml of dissolution medium.

For preparation of buffer, 1.36 g of $KH_2PO_4$ and 1 ml of TEA (triethylamine) was dissolved in 1000 ml water and pH was adjusted to 2.8 with orthophosphoric acid and acetonitrile used as a mobile Phase buffer.

Test samples were collected for analysis under chromatographic conditions by using Hypersil BDS C18 (250 mm×4.6 mm, 5 µm) column at a flow rate of 1.2 ml/min at column temperature of 25° C. of the injection volume 25 µm and run time of 20 min. Dissolution media was separately injected in equal volume as blank and standard preparation in six replicates and test preparation into the chromatograph. Chromatograms were recorded and responses were measured for major peaks.

| Enzalutamide oral solution | |
|---|---|
| Media | 0.3% CTAB in 0.1N HCl |
| Volume | 900 ml |
| USP apparatus | Type II (paddle) |
| RPM | 50 |
| Product of the present Invention (%) | |
| Assay (%) | 102.58 |
| SMUI (0.5%) | 0.042 |
| Total (0.2%) | 0.096 |
| pH | 6.5-6.89 |
| Time Dissolution (30 Minutes) | 103.43 to 106.63 (Min. to Max) |

Stability for the Product of the Present Invention

| Sr. No | Description | Initial | After 15 days 40° C./ 75% RH | After 1 month 40° C./ 75% RH | After 3 months 40° C./ 75% RH |
|---|---|---|---|---|---|
| 1. | Assay % | 99.98 | 98.80 | 98.32 | 98.48 |
| 2. | SMUI (0.5%) | — | 0.178 | 0.167 | 0.100 |
| 3. | Total (2.0%) | — | 0.238 | 0.248 | 0.255 |
| 4. | B.H.A % | 106.85 | 106.85 | 102.51 | 101.81 |
| 5. | B.H.T % | 102.51 | 102.51 | 99.01 | 93.62 |
| 6. | Ethanol Content % | — | — | — | 111.8 |
| 7. | Average Dissolution (After 30 minutes) | 103.43 | 103.50 | 104.60 | 103.44 |

The pharmaceutical dosage form prepared as per the present invention studied for its stability under accelerated stability analysis conditions. It was found to be adequately stable, as per general stability requirement under accelerated conditions.

The invention described herein comprises in various objects as mentioned above and their description in relation to characteristics, compositions and process adopted. While these aspects are emphasised in the invention, any variations of the invention described above are not to be regarded as departure from the spirit and scope of the invention as described.

What is claimed is:

1. A pharmaceutical composition in the form of an oral solution of enzalutamide, the composition comprising:
   (a) enzalutamide, in a concentration of from about 1% to about 5% by weight of the composition;
   (b) polyoxyl 35 castor oil, in a concentration of from about 25% by weight to about 90% by weight of the composition,
   (c) a stabilizer component comprising BHA and BHT, in a concentration of from about 0.01% by weight to about 5% by weight of the composition;
   (d) ethanol, in a concentration of from about 3% by weight to about 20% by weight of the composition;
   (e) polyethylene glycol 400, in a concentration of from about 10% by weight to about 39% by weight of the composition;
   (f) a sweetener component comprising at least one pharmaceutically acceptable sweetener, in a concentration of from about 0.04% by weight to about 10% by weight of the composition; and
   (g) a flavoring component comprising at least one pharmaceutically acceptable flavoring agent, in a concentration of in a concentration of from about 0.2% by weight to about 7% by weight of the composition.

2. A method of preparing the pharmaceutical composition of claim 1, the method comprising:
   (1) preparing a Solution A, wherein said Solution A is prepared by:
      (a) adding polyoxyl 35 castor oil to a reaction vessel, and heating polyoxyl 35 castor oil to a temperature of about 50° C. until it exhibits a clear appearance;
      (b) adding BHA and BHT to said reaction vessel, and stirring the resulting mixture continuously at a temperature of about 50° C.; and
      (c) adding enzalutamide to said reaction vessel, and stirring the resulting mixture continuously at a temperature of about 50° C. until it exhibits a uniform appearance;
   (2) preparing a Solution B comprising a sweetener and a flavoring agent dissolved in ethanol;
   (3) adding Solution B to Solution A and stirring the resulting mixture continuously at a temperature of about 50° C.;
   (4) adding polyethylene glycol 400 to the mixture of Solution B and Solution A, and stirring the product mixture continuously at a temperature of about 50° C. until it exhibits a uniform appearance; and
   (5) cooling the product mixture to room temperature, thereby obtaining an oral solution of enzalutamide.

3. The method of claim 2 wherein said enzalutamide is provided in the form of solid particles,
   said particles having a particle size distribution wherein the D90 is no less than 21 microns and no more than 80 microns.

* * * * *